(12) United States Patent
Krausz et al.

(10) Patent No.: US 11,530,976 B2
(45) Date of Patent: Dec. 20, 2022

(54) PARTICLE ANALYSIS METHOD AND APPARATUS FOR A SPECTROMETRY-BASED PARTICLE ANALYSIS

(71) Applicants: Max-Planck-Gesellschaft zur Foerderung der Wissenschaften e.V., Munich (DE); Ludwig-Maximilians-Universitaet Muenchen, Munich (DE)

(72) Inventors: Ferenc Krausz, Garching (DE); Ioachim Pupeza, Tuerkenfeld (DE); Mihaela Zigman Kohlmaier, Munich (DE); Marinus Huber, Munich (DE)

(73) Assignees: Max-Planck-Fesellschaft zur Foerderung der Wissenschaften e.V., Munich (DE); Ludwig-Maximilians-Universitaet Muenchen, Munich (DE)

( * ) Notice: Subject to any disclaimer, the term of this patent is extended or adjusted under 35 U.S.C. 154(b) by 102 days.

(21) Appl. No.: 17/269,174

(22) PCT Filed: Sep. 14, 2018

(86) PCT No.: PCT/EP2018/074933
§ 371 (c)(1),
(2) Date: Feb. 17, 2021

(87) PCT Pub. No.: WO2020/052785
PCT Pub. Date: Mar. 19, 2020

(65) Prior Publication Data
US 2021/0270719 A1      Sep. 2, 2021

(51) Int. Cl.
*G01N 15/14*      (2006.01)
*G01N 33/483*      (2006.01)
(Continued)

(52) U.S. Cl.
CPC ..... *G01N 15/1434* (2013.01); *G01N 15/1459* (2013.01); *G01N 33/4833* (2013.01);
(Continued)

(58) Field of Classification Search
CPC ........... G01N 15/1434; G01N 15/1459; G01N 33/4833; G01N 2015/0065;
(Continued)

(56) References Cited

U.S. PATENT DOCUMENTS 9,835,552 B2 * 12/2017 Wagner .............. G01N 21/3577
2008/0049213 A1 * 2/2008 Wada ..................... G01N 21/45
977/840

(Continued)

FOREIGN PATENT DOCUMENTS

| EP | 3023756 A1 | 5/2016 |
|---|---|---|
| EP | 3037805 A1 | 6/2016 |
| WO | 2018171869 A1 | 9/2018 |

OTHER PUBLICATIONS

Baker et al. (2014). Using Fourier transform IR spectroscopy to analyze biological materials. Nature Protocols, 9(8).
(Continued)

*Primary Examiner* — Roy M Punnoose
(74) *Attorney, Agent, or Firm* — Caesar Rivise, PC

(57) ABSTRACT

A particle analysis method and apparatus, including a spectrometry-based analysis of a fluid sample (1), comprises the steps of creating a sample light beam S and a probe light beam P with a light source device (10) and periodically varying a relative phase between the sample and probe light beams S, P with a phase modulator device (20), irradiating the fluid sample (1) with the sample light beam S, detecting the sample and probe light beams S, P with a detector device (40), and providing a spectral response of the at least one particle (3), wherein the light source device (10) comprises
(Continued)

at least one broadband source, which has an emission spectrum covering a mid-infrared MIR frequency range, and the phase modulator device (20) varies the relative phase with a scanning period equal to or below the irradiation period of irradiating the at least one particle (3, 4).

56 Claims, 5 Drawing Sheets

(51) Int. Cl.
  *G01N 15/00*    (2006.01)
  *G01N 15/10*    (2006.01)
(52) U.S. Cl.
  CPC .............. *G01N 2015/0065* (2013.01); *G01N 2015/1006* (2013.01); *G01N 2015/1454* (2013.01)
(58) Field of Classification Search
  CPC ... G01N 2015/1006; G01N 2015/1454; G01N 15/1429
  USPC .................................................. 356/326, 336
  See application file for complete search history.

(56) References Cited

U.S. PATENT DOCUMENTS

| | | | |
|---|---|---|---|
| 2009/0219544 A1* | 9/2009 | Joo | G01B 9/02091 356/451 |
| 2017/0350803 A1 | 12/2017 | Jalali et al. | |
| 2020/0033259 A1 | 1/2020 | Krausz et al. | |

OTHER PUBLICATIONS

Bartels et al. (2007). Ultrafast time-domain spectroscopy based on high-speed asynchronous optical sampling. Review of Scientific Instruments, 78, 035107-1-035107-8.

Bassan et al. (2010). Resonant Mie Scattering (RMieS) correction of infrared spectra from highly scattering biological samples. Analyst, 135, 268-277.

Coddington et al. (2010) Coherent dual-comb spectroscopy at high signal-to-noise ratio. Physical Review A, 82, 043817-1-043817-13.

Hadjiloucas et al. (2009). High signal to noise ratio THz spectroscopy with ASOPS and signal processing schemes for mapping and controlling molecular and bulk relaxation processes. Journal of Physics: Conference Series, 183, 1-6.

Martin et al. (2010). Distinguishing cell types or populations based on the computational analysis of their infrared spectra. Nature Protocols, 5(11), 1748-1760.

Shim et al. (2006). Femtosecond pulse shaping directly in the mid-IR using acousto-optic modulation. Optics Letters, 31(6), 838-840.

Urbanek et al. (2016). Femtosecond terahertz time-domain spectroscopy at 36 kHz scan rate using an acousto-optic delay. Applied Physics Letters, 108, 121101-1-121101-5.

Vaccari et al. (2012). Infrared Microspectroscopy of Live Cells in Microfluidic Devices (MDIRMS): Toward a Powerful Label-Free Cell-Based Assay, Analytical Chemistry, 84.

International Search Report for PCT/EP2018/074933 dated May 28, 2019.

* cited by examiner

PARTICLE ANALYSIS METHOD AND APPARATUS FOR A SPECTROMETRY-BASED PARTICLE ANALYSIS

CROSS-REFERENCE TO RELATED APPLICATIONS

This application is a U.S. National Phase Application of PCT/EP2018/074933, filed Sep. 14, 2018, the contents of which application are incorporated herein by reference in their entireties for all purposes.

FIELD OF THE INVENTION

The invention relates to a particle analysis method, including a spectrometry-based analysis of a flowing fluid sample with at least one particle to be analyzed, in particular at least one biological particle, like a biological cell or a component thereof. In particular, the invention relates to a particle analysis method allowing the provision of diagnostically relevant information. Furthermore, the invention relates to a particle analysis apparatus for spectrometry-based analysis of a flowing fluid sample with at least one particle. Applications of the invention are available in the fields of biology, medicine, in particular medical diagnostics and therapy, and biochemistry, in particular in rapid infrared spectroscopy measurements for flow cytometry. The particle analysis apparatus can be used as a particle classification and/or detection apparatus, in particular as a cell classification and/or detection apparatus.

TECHNICAL BACKGROUND

In the present specification, reference is made to the following prior art illustrating the technical background of the invention:
[1] U.S. Pat. No. 9,835,552 B2;
[2] EP 3 037 805 A1;
[3] PCT/EP2017/056705 (not published on the priority date of the present specification);
[4] P. Bassan et al. in "Analyst" 135.2 (2010): 268-277;
[5] M. J. Baker et al. in "Nature protocols" 9.8 (2014): 1771;
[6] F. L. Martin et al. in "Nature protocols" 5.11 (2010): 1748;
[7] B. Urbanek et al. in "Applied Physics Letters" 108.12 (2016): 121101;
[8] S. Hadjiloucas, et al. in "Journal of Physics: Conference Series" Vol. 183. No. 1. IOP Publishing, 2009;
[9] EP 3 023 756 A1;
[10] A. Bartels et al. in "Review of Scientific Instruments" 78, 035107 (2007);
[11] I. Coddington et al. in "Phys. Rev. A" 82, 043817 (2010);
[12] L. Vaccari, et al. in "Analytical chemistry" 84.11 (2012): 4768-4775; and
[13] F. L. Martin, et al. in "Nature protocols" 5.11 (2010): 1748.

In modern molecular biology, experimental medicine or medical diagnostics, there is an interest in robust information-rich measurements of biological samples, like individual cells, cell aggregates, cell components or other particles, at single-particle resolution. Typically, those measurements can be obtained on the basis of spectrometric techniques for investigating interactions of the sample with light in the mid-infrared (MIR) spectral range.

An example of a generally known, highly sensitive spectrometric technique is Fourier transform (FTIR) spectrometry, which allows collecting MIR spectra with high specificity and without the need of labelling the particles to be analyzed with a marker substance. Single-particle resolution can be obtained by combining FTIR spectrometry with microscopy in an FTIR microscope. Advantageously, broadband infrared (IR) spectroscopic measurements on single-cell level can in principle provide most of the desired information in a label-free fashion. However, conventional FTIR spectrometry has a substantial disadvantage in terms of its limited sensitivity and scanning speed. With practical applications, it can be estimated that e. g. one cell per second can be spectrometrically analyzed with an FTIR microscope. However, large amounts of cells require essentially higher measuring speeds, as obtained in high-throughput screening methods.

A widespread and powerful technique for the measurement of cellular characteristics and states (phenotype) with measuring speed is conventional flow cytometry. It is highly applicable to the study of cellular populations and identification of rare cellular (sub-)populations, due to its high-throughput and multi-parametric nature. However, flow cytometry is based on image recognition techniques or the use of targeted dyes, predominantly fluorophores, applied to the particles to be analyzed. The image recognition techniques are time consuming, and they have a limited specificity. The use of dyes and characterization of previously identified molecular markers is another inherent limitation of flow cytometry, which furthermore may have particular disadvantages as the sample has to be processed before the actual examination by using dyes as markers and the dyes may change the biological behaviour of the cells, so that they cannot be used for further investigations.

The conventional FTIR spectrometry could not be combined with high-throughout flow cytometry, as FTIR spectrometry is too slow and not sensitive enough for measuring flowing samples. Furthermore, coupling broadband IR spectroscopy to high-throughput measurements in cytometric systems would require fast spectral acquisition with sufficiently high signal-to-noise ratio (SNR). This especially problematic in the MIR region (between 1000 $cm^{-1}$ and 3000 $cm^{-1}$), where strong water absorption is a problem and ultrasensitive and fast spectrometers with a broad spectral coverage are currently not available.

An attempt to overcome this limitation and for combining the advantages of flow cytometry with a sensitive, label-free interferometric spectroscopic detection has been described in [1]. Interferometric spectroscopic measurements of particles utilize an IR light beam that is split into two beams. Only one of the IR light beams is directed through a measurement volume including the sample. Subsequently, the beams are recombined and detected. The phase differential between the beams provides destructive interference when no particle is in the measurement volume. With a particle, e. g. a living cell, in the measurement volume, a change is detected, which results from an MIR absorption or scattering by the particle.

However, the spectroscopic detection of [1] has the following drawbacks, resulting in a restricted applicability of this technique. Firstly, the IR light beam is created with one or more quantum cascade lasers (QCLs), each having a narrow emission wavelength being matched to one spectral feature, like absorption peak, expected in the particles to be analyzed. Furthermore, the light detection system is not adapted for measuring the spectral response of a traversing particle. Therefore, the spectroscopic detection does not allow the collection of MIR spectra or even molecular fingerprints, resulting in a limited specificity and allowing the detection of pre-known particles only. For detecting changing cells types, the set-up has to be readjusted for matching the emission wavelengths. The technique of [1] does not disclose a way how to achieve a spectrally resolved measurement of the sample if only one QCL is used. A spectrally resolved measurement with an appropriate number of spectral elements would require a corresponding number of QCLs (at different wavelengths) each in combination an associated detector. Secondly, in addition to the reduced information content of the measurement, if the technique of [1] would be used for detecting multiple spectral elements, it would require a large number of QCLs and the same number of detectors, resulting in a very expensive configuration with a complex bulky geometry.

Further highly sensitive interferometric MIR spectroscopy techniques have been described in [3]. However, these techniques have been applied with resting samples, provided e. g. in a cuvette only, so that the use of slow phase modulators was sufficient for the interferometric detection.

OBJECTIVE OF THE INVENTION

The objectives of the invention are to create an improved particle analysis method and an improved particle analysis apparatus, providing a spectrometry-based analysis of a flowing fluid sample with at least one particle to be analyzed, being capable of avoiding disadvantages of conventional techniques. In particular, the particle analysis is to be obtained with increased sensitivity, specificity and/or measuring speed compared with the conventional techniques.

SUMMARY OF THE INVENTION

These objectives are correspondingly solved by a particle analysis method and a particle analysis apparatus of the invention.

According to a first general aspect of the invention, the above objective is solved by a particle analysis method, wherein a fluid sample comprising a sheath fluid and at least one particle to be analyzed is spectrometrically investigated for providing a spectral response of the at least one particle. The sheath fluid comprises e. g. water or a cell cultivation liquid. The fluid sample comprises e. g. a watery suspension of particles, a suspension including biological cells or blood serum.

A sample light beam and a probe light beam are created with a common light source device. The initially created light fields of the sample light beam and the probe light beam are coherent. The fluid sample is irradiated with the sample light beam, while the fluid sample is flowing in at least one sample channel, like a flow-through cuvette, through a beam path of the sample light beam. The measurement is conducted while the fluid sample is moving along the at least one sample channel, in particular the at least one particle to be analyzed is traveling across the sample light beam path (beam path of the sample light beam) under the effect of a directed flow force within the sample channel. If only one sample channel is used, the fluid sample is irradiated with one sample light beam, and if multiple sample channels are used in parallel, the fluid sample is irradiated in the sample channels with partial sample light beams split from a common sample light beam. The fluid sample is irradiated such that the at least one particle occurring in the sample light beam path is irradiated for a predetermined irradiation period (time of interaction of the particle with the light). The irradiation period is determined by the size and velocity of the particle and the diameter of the sample light beam at the position of irradiation in the sample channel.

A relative phase between a phase (light field phase) of the sample light beam and a phase of probe light beam is periodically changed with a phase modulator device acting on at least one of the sample and probe light beams. Preferably, the phase modulator device is arranged in a beam path of the probe light beam. Preferably, the beam path of the probe light beam does not include a fluid sample or a sample channel. After the interaction of the sample light beam with the fluid sample, the sample and probe light beams are superimposed and commonly detected with a detector device (MIR light detection device). The detector device generally is configured for interferometrically sensing a phase of the combined sample and probe light beams. Depending on the sensing principle, various setups of the detector device are available as outlined with reference to the embodiments below. If multiple sample channels are used, the detector device may comprise multiple detector units each being assigned to one of the sample channels. Furthermore, if multiple sample channels are used, multiple probe light beams or one common probe light beam can be used for sampling the partial sample light beams.

The detector device provides an output (output signal) representing a coherent superposition of the combined sample and probe light beams. Based on an output of the detector device, a spectral response of the at least one particle is created, preferably by comparing the output signal collected with the irradiated sample with a reference signal of the sheath fluid alone. The spectral response (spectrally resolved response) comprises an absorption and/or phase spectrum of the at least one particle. The term absorption spectrum covers all types of spectra being determined by the light absorption in the particle, in particular absorption or reflection spectra. The spectrum is the function of the absorption and/or phase of the wave number (or wavelength). The spectrum is a continuous spectrum or quasi-continuous spectrum, including a plurality of spectral lines (or: spectral elements) covering the spectral range of particle-light interaction. Preferably, the spectrum includes at least 50 spectral elements, e. g. 100 spectral elements or more, like at least 500 spectral elements or even up to 1000 spectral elements.

According to the invention, the light source device comprises at least one broadband source, which has an emission spectrum covering a mid-infrared (MIR) frequency range. At least the sample light beams created by the light source device have a primary emission spectrum covering a spectral range, which allows the excitation of vibrational and/or rotational transitions in sample components, in particular organic molecules included in the fluid sample. Due to the broadband emission spectrum, the spectral response of the sample can be detected like a specific spectral band pattern (spectral or molecular "fingerprint"). The spectral response is specific for sample components in terms of the spectral positions of spectral bands in the spectral band pattern and the relative intensities of the spectral bands. This is in contrast to the technique of [1], wherein one or some spectral line(s) of OCL(s) are used, which are not capable to provide a continuous or quasi-continuous coverage of an emission spectrum. Advantageously, utilizing at least one broadband source allows the provision of the spectral response comprising the absorption and/or phase spectrum of the at least one particle. Deviating from [1], it is not necessary to match the light source emission to expected spectral bands, and the sample can be investigated without pre-knowledge on particle spectra. Preferably, the emission spectrum covers a frequency interval within a frequency range from 100 cm$^{-1}$ to 4000 cm$^{-1}$. Within this frequency range, the frequency interval may cover an energy difference of at least 30 cm$^{-1}$ (thus allowing the spectral separation of at least two bands within a spectrum), preferably at least 100 cm$^{-1}$, e.g. 400 cm$^{-1}$ or more. For example, the frequency interval may cover a range from 1000 cm$^{-1}$ to 1400 cm$^{-1}$ (covering typical spectral bands of carbohydrates and nucleic acids), a range from 1400 cm$^{-1}$ to 1800 cm$^{-1}$ (covering typical spectral bands of amines or proteins, in particular amide I/II bands are main absorption features of proteins) and/or a range from 3000 cm$^{-1}$ to 3700 cm$^{-1}$ (covering typical spectral bands of lipids). For example, with a frequency interval from 1000 cm$^{-1}$ to 1800 cm$^{-1}$, spectral bands of carbon hydrates and amines/proteins can be investigated (see e. g. [5]).

Furthermore, according to the invention, the phase modulator device varies the relative phase (phase difference, relative phase delay) of the sample and probe light beams for a controlled change of the relative phase with a scanning period (time interval of a complete variation of the relative phase, required for collecting the spectral response of the particle) equal to or below the irradiation period of irradiating the at least one particle. Advantageously, the inventors have found, that light source devices with sufficient output power and phase modulator devices with sufficient high modulation frequency are available for collecting all interferometric information during the occurrence of the particle in the beam path of the sample light beam. The rapid and controlled change of the relative phase delay between sample and probe light beams ensures, that the optical spectrum can be obtained on time scales smaller than the time the particle needs to travel through the measurement volume. Furthermore, rapid measurements enable an increase of the flow speed of particles in the system and thereby the throughput. Advantageously, up to 30.000 spectra per second can be collected with the inventive technique.

Conventional interferometric techniques utilize relative phase modulation between the light beams travelling in the interferometer arms for minimizing the effect of mechanical noise sources on the detector signal. For this purpose, a relatively slow phase modulation with scan frequencies up to 10 Hz was sufficient. On the contrary, the phase modulation frequency used with the invention is selected for sensing spectra of moving particles. The phase modulation frequency is selected in dependency on the size and velocity of the particle(s) and the diameter of the sample light beam at the position of irradiation in the sample channel, e. g. in a range above 1 kHz. Furthermore, the phase modulation amplitude used with the invention is selected such that the emission spectrum covering the mid-infrared (MIR) frequency range is sampled with a spectral resolution, which allows an identification of the spectral features of the particle to be analyzed. The spectral resolution is preferably at least 16 cm$^{-1}$.

According to a preferred application of the invention, at least one particle property of the at least one particle is determined based on the spectral response of the at least one particle. Advantageously, the spectral response of the at least one particle is analyzed for a direct output of the particle property. The term "particle property" refers to any feature specifically determining the spectral response and chemically and/or physically characterizing the particle. With preferred examples, the particle property may comprise a chemical feature, like a chemical composition of the particle or the occurrence of chemical substances, a physical feature, like a size or shape of the particle, and/or a particle type, in particular a cell type of a biological cell, like a characterization as a healthy cell or a tumour cell or a stem cell. With regard to detecting the physical feature, the particle size will influence the spectral response via MIE scattering (see [4]), and that this may be used to determine the size and/or shape of the particle. Alternatively or additionally, the particle property may comprise a change of the chemical and/or physical feature. The term "particle property" also may include the spectral response of the at least one particle as such.

Determining the at least one particle property from the spectral response comprises e. g. a calculation based on and/or a comparison with predetermined calibration data obtained with known particles. For example, characteristics of the spectral response, like a spectrum shape and/or intensity can be input in a numerical statistical evaluation or a machine learning algorithm resulting in the particle property to be obtained. Advantageously, the particle analysis of the invention is capable of a real time characterization of moving particles, thus combining for the first time the advantages of flow cytometry with a measurement of spectra of the particles.

The at least one particle property of the at least one particle can be determined based on the spectral response, as in the irradiation period of irradiating the at least one particle, a spatially integrated (or moderately spatially resolved) measurement of the particle's spectral response is carried out, and the particles can be distinguished on the basis of the spectral responses. As an example, it is possible that different cell types (e.g. cancer vs. normal cells) have a characteristic concentration ratio of certain molecule groups (e.g. proteins vs lipids) due to their different structure and can thus be differentiated. Thus, the particle property determined is cell type of the particle. Further examples can be found e. g. in [12] or [13].

According to a second general aspect of the invention, the above objective is solved by a particle analysis apparatus, being configured for a spectrometry-based analysis of a fluid sample comprising a sheath fluid and at least one particle to be analyzed, and comprising a light source device being configured for creating a sample light beam and a probe light beam, a phase modulator device being configured for periodically varying a mutual relative phase between the sample and probe light beams, at least one sample channel for accommodating a flow of the fluid sample and for irradiating the fluid sample with the sample light beam, so that the at least one particle is irradiated for a predetermined irradiation period, and a detector device being configured for detecting the sample and probe light beams and providing a spectral response of the at least one particle. According to the invention, the light source device comprises at least one broadband source, which has an emission spectrum covering a mid-infrared (MIR) frequency range, the phase modulator device is configured for varying the relative phase with a scanning period equal to or below the irradiation period of irradiating the particles, and the particle analysis apparatus, e. g. a calculation device included therein, is further configured for providing a particle property of the at least one particle on a basis of the spectral response of the at least one particle. Preferably, the particle analysis apparatus is adapted for conducting the particle analysis method according to the first general aspect of the invention.

Advantageously, the invention discloses methods and devices that allow to rapidly measure a broadband absorption (and/or phase) spectrum with high SNR of individual particles (e.g. biological cells or cell aggregates or cell components or organic macromolecules, or non-biological organic or non-organic particles, e. g. in environmental analyses) passing by in the sample channel, like e. g. a flow-through cuvette, in a high-throughput manner. Preferably, the particle analysis of the fluid sample comprises a high-throughput measurement. For biological application, preferably at least 1000 cells are analysed per second. The invention provides a unique opportunity to access a change in molecular composition (by acquisition of the absorption and/or phase spectrum) to identify physiological differences at cellular level. Ultra-broadband infrared spectroscopy inherently enables quantitative multi-parametric identification of different cellular states, cellular conditions and cell types based on simultaneous evaluation multiple cellular hallmarks culminating in cellular phenotypes. In combination with the high-throughput capabilities of the device, this sets the basis for different applications, like label free cell-type identification, label free phenotype identification, label free cell sorting, and/or identification of tumour cells in blood of a biological organism, e. g. a patient.

According to a particularly preferred application of the invention, the fluid sample comprises a biological sample from a human or animal organism. The sample is collected from the organism before the application of the inventive method. Subsequently, after the application of the inventive method, at least a part of the sample can be re-introduced to the organism. Collecting and re-introducing the sample from and to the organism is not a part of the inventive method. Medical tools being configured for collecting and re-introducing the sample from and to the organism can be components of the inventive particle analysis apparatus. The spectral response of the biological fluid sample is measured for obtaining diagnostically relevant information on the organism. The term "diagnostically relevant information" refers to any information on the sample, in particular the composition thereof, differences compared with reference samples or temporal changes of the sample, which can be used for subsequently providing or validating a medical diagnosis. Accordingly, with a preferred embodiment of the invention, the particle analysis method includes the step of evaluating the spectral response of the sample in order to obtain the diagnostically relevant information. In terms of device features, a preferred embodiment of the particle analysis apparatus preferably includes a calculation device, which is adapted for processing the spectral response and providing the diagnostically relevant information. Advantageously, the diagnostically relevant information can be output to a user of the inventive technique, e. g. a doctor. Subsequently, the user can provide a diagnosis in consideration of the diagnostically relevant information.

According to an advantageous embodiment of the invention, the detector device is configured for a field-resolved detection of the sample light beam by electro-optical sampling (in the following: FRS embodiment). Field-resolved detection (also indicated as time domain spectroscopy, in particular in THz range) of the sample light beam, wherein the probe light beam is utilized for the electro-optical sampling of the sample light beam, provides substantial advantages in terms of a temporal resolution of the spatial flow of particles and a broadband detection capability. Preferably, field-resolved detection is conducted a disclosed in [2], which is introduced into the present specification by reference, in particular with regard to the configuration of a detector device for the field-resolved detection of the sample light beam and the signal read-out.

According to a first variant of the FRS embodiment, the light source device comprises a laser source, preferably a pulsed laser source, coupled with an MIR generation device. The MIR generation device generally comprises an optical device converting an input laser beam into an output laser beam having the emission spectrum, which covers the mid-infrared (MIR) frequency range. The MIR generation device preferably includes an optically non-linear component being arranged for creating the emission spectrum based on difference frequency generation. Utilizing the MIR generation device has advantages in terms of creating the emission spectrum having a broadband characteristic with a single MIR generation device output.

Firstly, an output of the laser source is split with a beam splitter device into a first interferometer arm including the MIR generation device and the sample channel, and a second interferometer arm including the phase modulator device. The sample light beam is created by the output of the MIR generation device, and the sample is irradiated with the sample light beam in the first interferometer arm. The probe light beam is created with the laser source, and it is directed along the second interferometer arm to the phase modulator device included in the second interferometer arm. The relative phase between the sample and probe light beams is controlled with the phase modulator device. After the interaction of the sample light beam with the fluid sample, both of the sample and probe light beams are recombined and directed to the detector device for the field-resolved detection of the sample light beam. The interaction of the sample light beam with the fluid sample includes an irradiation of particles traveling in the sample channel or irradiating the sheath fluid for a reference measurement as described below.

With the first variant of the FRS embodiment of the invention, the phase modulator device preferably comprises an acousto-optical delay line or a mechanical phase modulator, like a sonotrode, having a modulation frequency of at least 500 Hz. Particularly preferred, the phase modulator device has a modulation frequency of at least 1 kHz, e. g. up to 30 kHz or even more. Alternatively, the phase modulator device may comprise a dazzler or a plunger coil coupled with a deflection mirror. Advantageously, compared with the mirror block utilized in [1] for setting static path length differences, these types of phase modulator device allow the interferometric measurement with essentially increased modulation frequencies.

According to a second variant of the FRS embodiment, the light source device comprises a first pulsed laser source and a second pulsed laser source (dual frequency comb or dual oscillator embodiment). The first and second pulsed laser sources are coupled via a repetition rate control device, which simultaneously provides the phase modulator device (asynchronous optical sampling embodiment). Alternatively, the first and second pulsed laser sources are coupled via a repetition rate and carrier-envelope offset phase control device, providing the phase modulator device (dual-comb-spectroscopy embodiment). The first pulsed laser source preferably is coupled with an MIR generation device creating the sample light beam. Thus, the sample light beam is created with the first pulsed laser source, preferably in combination with the MIR generation device, with a first repetition rate and directed via the sample channel to a beam combiner device. The probe light beam is created with the second pulsed laser source with a second, different repetition rate and directed directly to the beam combiner device. The relative phase between the sample and probe light beams is controlled with the repetition rate control device or the repetition rate and carrier-envelope offset phase control device. The repetition rate difference is selected with reference to the repetition rate of one of the laser sources such that the spectral response can be detected in the whole spectral range to be investigated. Subsequent to the interaction of the sample light beam with the fluid sample, the sample and probe light beams are recombined with the beam combiner device and input to the detector device for the field-resolved detection of the sample light beam. This embodiment of the invention has advantages resulting from a facilitated setting of the relative phase with the repetition rate control device and the capability of obtaining high modulation frequencies.

According to a further advantageous embodiment of the invention, the detector device is configured for a multi-heterodyne detection of the sample light beam in the MIR frequency range (in the following: multi-heterodyne embodiment). In this case, particular advantages result from the simple structure of IR sensors included in the detector device.

According to a first variant of the multi-heterodyne embodiment, the light source device comprises a laser source coupled with an MIR generation device. The MIR generation device has the advantageous configuration as noted above with reference to the first variant of the FRS embodiment. An output of the laser source or the MIR generation device is split with a beam splitter device into a first interferometer arm including the sample channel and a second interferometer arm including the phase modulator device. The sample light beam being created with the laser source and the MIR generation device irradiates the sample in the first interferometer arm. The probe light beam is provided by the output of the laser source or the MIR generation device, and is directed along the second interferometer arm including the phase modulator device. The relative phase between the sample and probe light beams is controlled with the phase modulator device. After the interaction of the sample light beam with the sample, the sample and probe light beams are recombined with a beam combiner device for the multi-heterodyne detection of the sample light beam in the MIR frequency range.

According to a second variant of the multi-heterodyne embodiment, the light source device comprises multiple MIR lasers. Each MIR lasers comprises e. g. one or more QCLs each having an output spectrum covering at least 20 cm$^{-1}$. With currently available QCLs, the light source device comprises at least 6 QCLs. Advantageously, the complexity of the optical setup can be reduced with this embodiment of the invention. An output of the MIR lasers is split with a beam splitter device into a first interferometer arm including the sample channel and a second interferometer arm including the phase modulator device. The sample light beam is created with the MIR lasers, and the sample is irradiated in the first interferometer arm, while the probe light beam is provided by the light split off the superimposed output of the MIR lasers. The relative phase between the sample and probe light beams is controlled with the phase modulator device in the second interferometer arm. After the interaction of the sample light beam with the sample, the sample and probe light beams are recombined for the multi-heterodyne detection of the sample light beam in the MIR frequency range.

Preferably, the phase modulator device employed with the multi-heterodyne embodiment of the invention is configured as described above with reference to the FRS embodiment of the invention.

According to a third variant of the multi-heterodyne embodiment, the light source device comprises a first pulsed laser source coupled with a first MIR generation device for creating the sample light beam and a second pulsed laser source coupled with a second MIR generation device for creating the probe light beam. This embodiment of the invention is adapted for providing the spectral response of the at least one particle by dual-comb-spectroscopy. In this case, the phase modulator device comprises a repetition rate and carrier-envelope offset phase control device coupled with the first and second pulsed laser sources. The relative phase and the carrier-envelope offset phase between the sample and probe light beams is controlled with the repetition rate and carrier-envelope offset phase control device, as described with reference to the second variant of the FRS embodiment. After the interaction of the sample light beam with the fluid sample, the sample and probe light beams are recombined for the multi-heterodyne detection of the sample light beam in the MIR frequency range. Similar to the FRS embodiment, this variant of the multi-heterodyne embodiment of the invention has advantages resulting from a facilitated setting of the relative phase with the repetition rate and carrier-envelope offset phase control device and the capability of obtaining high modulation frequencies.

If according to a further preferred embodiment of the invention, a reference measurement is conducted, a spectral reference response of the sheath fluid can be detected and compared with the output signal collected with the irradiated particle for providing the at least one particle property. The step of irradiating the fluid sample with the sample light beam additionally includes irradiating the sheath fluid for the predetermined irradiation period. The sheath fluid is irradiated and the interferometrically superimposed sample and probe light beams are detected with the detector device when no particle is present in the light path of the sample light beam. The sheath fluid can be irradiated once for obtaining reference data, or it can be irradiated simultaneously with the irradiation of the at least one particle. The spectral reference response of the sheath fluid is provided, based on an output of the detector device. The spectral reference response can be used as a reference for the spectral response of the particle. For example, the spectral response of the particle can be divided by the spectral reference response, or the spectral reference response can be subtracted from the spectral response of the particle. Alternatively, spectral reference response can be used in the calculation of the at least one particle property. Advantageously, the reference measurements improves the sensitivity and reproducibility of the particle analysis.

The reference measurement can be conducted by irradiating the fluid sample at two different irradiation positions being separated from each other along the sample channel, so that a particle can be in at most one position of the two irradiation positions. Advantageously, this reference measurement allows a particle measurement and a reference measurement at the same time, and the reference measurement simply can be implemented by directing two copies of the sample light beam to the displaced irradiation positions and sensing the spectral response of the particle and the spectral reference response with two detector units of the detector device. Preferably, the irradiation positions are separated by a spacing equal to 1 to 2 diameters of the particle to be analyzed or by the beam diameter of the two sample light beams (whatever is larger). Advantageously, each particle can be detected at each of the subsequent irradiation positions, while the measurement at the other of the irradiation positions is used for the reference measurement. With this double detection, the SNR of the particle analysis can be improved.

Alternatively, the reference measurement can be conducted at two irradiation positions being included in different sample channels being connected in parallel.

Advantageously, a multiple sample channels can be used not only for the reference measurement, but also for an increased throughput of the particle analysis. Multiple (at least two) sample channels can be connected in parallel, i. e. upstream ends of the sample channels can be connected with a common input channel or a common fluid sample reservoir. Alternatively, multiple (at least two) sample channels can be provided each being connected with a separate fluid sample reservoir. Downstream ends of the sample channels can be connected with separate output channels, a common output channel, a collection reservoir, a sorting device or any other device for subsequent fluid processing. Partial sample light beams are split from a common initial sample light beam and directed to the sample channels. The detector device comprises multiple detector units each being assigned to one of the sample channels and being preferably operated according to one of the FRS and multi-heterodyne embodiments.

The parallel measurement includes flowing the fluid sample through a first sample channel and at least one further sample channel, e. g. being connected in parallel relative to the first sample channel, and irradiating the fluid sample with the partial sample light beams via split sample light beam paths of the sample light beam. Accordingly, a first particle occurring in the sample light beam path of the first channel is irradiated for a predetermined irradiation period and at least one further particle occurring in the sample light beam path of the at least one further sample is irradiated for a predetermined irradiation period. Preferably, equal irradiation periods are applied in the sample channels. After the interaction with the fluid sample in the sample channels, the partial sample light beams are recombined with the probe light beam. The superimposed light field of the sample and probe light beams of the first and at least one further sample channels is detected with the detector device. Based on the output of the detector device, multiple spectral responses of the particles detected in the sample channels are obtained, and the particle properties of the first and at least one further particle is determined from spectral responses of the first and at least one further particles.

Additionally to the advantageous increased throughput, the parallel measurement can be utilized for comparing particles in the sample channels. According to this variant of the invention, a differential spectral response from the first spectral response and a second spectral response of the particles is provided. The differential spectral response can be used in the step of providing the particle property for detecting altered particles, e. g. biological cells being changed from a disease. Furthermore, the differential spectral response can be utilized for implementing the reference measurement.

According to a further advantageous embodiment of the invention, the sample light beam (or the partial sample light beams) irradiating the sample has an output power equal to or above 0.1 mW, in particular equal to or above 1 mW. For increasing the SNR with high throughput measurements, the output power preferably is increased above 10 mW, up to 100 mW or even higher. As an example, an output power in a range from 80 mW to 120 mW is preferred for detecting 1000 cells per second.

Preferably, the at least one broadband source of the light source device is stably operated and the fluid sample is investigated in a continuous operation mode. The output power of the light source device is stabilized with a control loop based stabilization device. Advantageously, the measurement with the flowing sheath fluid surrounding the particles allows a continuous measurement without heating of the particles. This has particular advantages for blood screening applications of the invention with biological cells, wherein at least some of the biological cells are to be re-introduced into an organism after the particle analysis.

According to a further preferred embodiment of the invention, the particles have a cross-sectional dimension, e. g. diameter, below 100 µm. Thus, advantages for flowing the fluid sample through a sample channel with a channel height substantially equal to or below 100 µm are obtained so that deteriorating absorptions by the sheath fluid, including water, can be avoided. Particularly preferred, the particles have a cross-sectional dimension below 40 µm.

Preferably, the particle analysis apparatus includes a control device which is configured for controlling the components of the particle analysis apparatus. The control device may comprise separate control units or one common control unit, e. g. computer circuits, being arranged for controlling the light source device, the phase modulator device, the detector device and the sample flow through the sample channel.

For setting the sample flow through the sample channel, a flow drive device is preferably provided. The flow drive device is configured for fluid sample and particle handling, including controlling at least one of time of flowing the fluid sample through the sample channel, flow velocity of the fluid sample through the sample channel, and density of particles within the fluid sample. Particularly preferred, the fluid sample has a flow velocity in a range from 0.1 mm/s to 100 mm/s, like e. g. 5 mm/s to 20 mm/s.

According to a further advantageous embodiment of the invention, the particle analysis method includes a step of sorting the particles in dependency on the spectral response or the particle property thereof. The particle analysis apparatus, preferably the fluidic device thereof, preferably is coupled with a particle sorting device being coupled with the detector device and/or the calculation device. The particle sorting device comprises a particle deflector, applying e. g. flow forces or dielectrophoretic forces on the particles, arranged at a channel branching. In dependency on a detected particle property, a particle can be deflected in one of multiple separate channels. Advantageously, particle sorting allows a recovery of rare particles, like rare cells from the fluid sample.

The inventive particle analysis method can be combined with at least one additional flow cytometry measurement being adapted for sensing particles with visible or UV light (e.g. forward and/or side scattering measurements and/or fluorescence measurements, using visible or UV lasers and detectors). The particle analysis apparatus can include at least one additional flow cytometry measurement set-up, which can be arranged for detecting particles upstream and/or downstream of the irradiation position of the inventive particle analysis. Advantageously, this embodiment allows gaining additional information, like particle size or the presence of fluorescent labels. This additional information can be used for an additional classification of the particles and/or for controlling the inventive particle analysis.

BRIEF DESCRIPTION OF THE DRAWINGS

Further details and advantages of the invention are described in the following with reference to the attached drawings, which schematically show in.

PREFERRED EMBODIMENTS OF THE INVENTION

Key-aspects of the invention are the ability to perform broadband, temporally and/or spectrally resolved optical measurements of sample particles (e.g. living cells) in a liquid medium in the infrared with high signal-to-noise ratio on very short time-scales (milliseconds and below). This allows to achieve the following four advantageous features of the invention, which are described with further details below:

1. Broadband (e.g. from 1000-3000 $cm^{-1}$ or another range as cited above) sample light beam that allow fast measurements with sufficient SNR, in particular for high throughput performance;
2. Methods and devices that allow to introduce and rapid and controlled change of the relative phase delay between the sample light beam and a probe light beam (in particular, the probe light beam can be either a portion/copy of the output of a laser source creating the sample light beam or a beam created by a second laser system coupled with the laser source creating the sample light beam;
3. Fast and sensitive light detection scheme, in particular with fast read-out electronics and data handling;
4. Liquid and particle handling system that allows to introduce particles into a measurement volume within a flow-through cuvette at a defined times and speed.

Preferred embodiments of the invention are described in the following with particular reference to the creation of the sample and probe light beams with a varying relative phase. Details of the laser setup, in particular controlling and stabilizing fs laser or operation frequency converters, are not described as they are known per se. Exemplary reference is made to transmission measurements, wherein the sample light beam passes through the sample channel. Alternatively, reflection measurements can be done in an analogue way by arranging the detector device on the irradiation side of the sample channel. As a further alternative, instead of a reflection measurement, a measurement of MIR radiation scattered at the particle could be conducted. In this case, the optics would be configured in such a way that a part of the sample beam, scattered at a certain angle (e.g. back reflex), is measured by the detector device. Furthermore, exemplary reference is made to the use of one or two sample light beams. With the parallel and/or reference measurements, more than two sample light beams can be used. While the phase modulation is introduced in the described embodiments in the second interferometer arm, alternatively or additionally phase modulation can introduced in the first interferometer arm.

Figure 1:
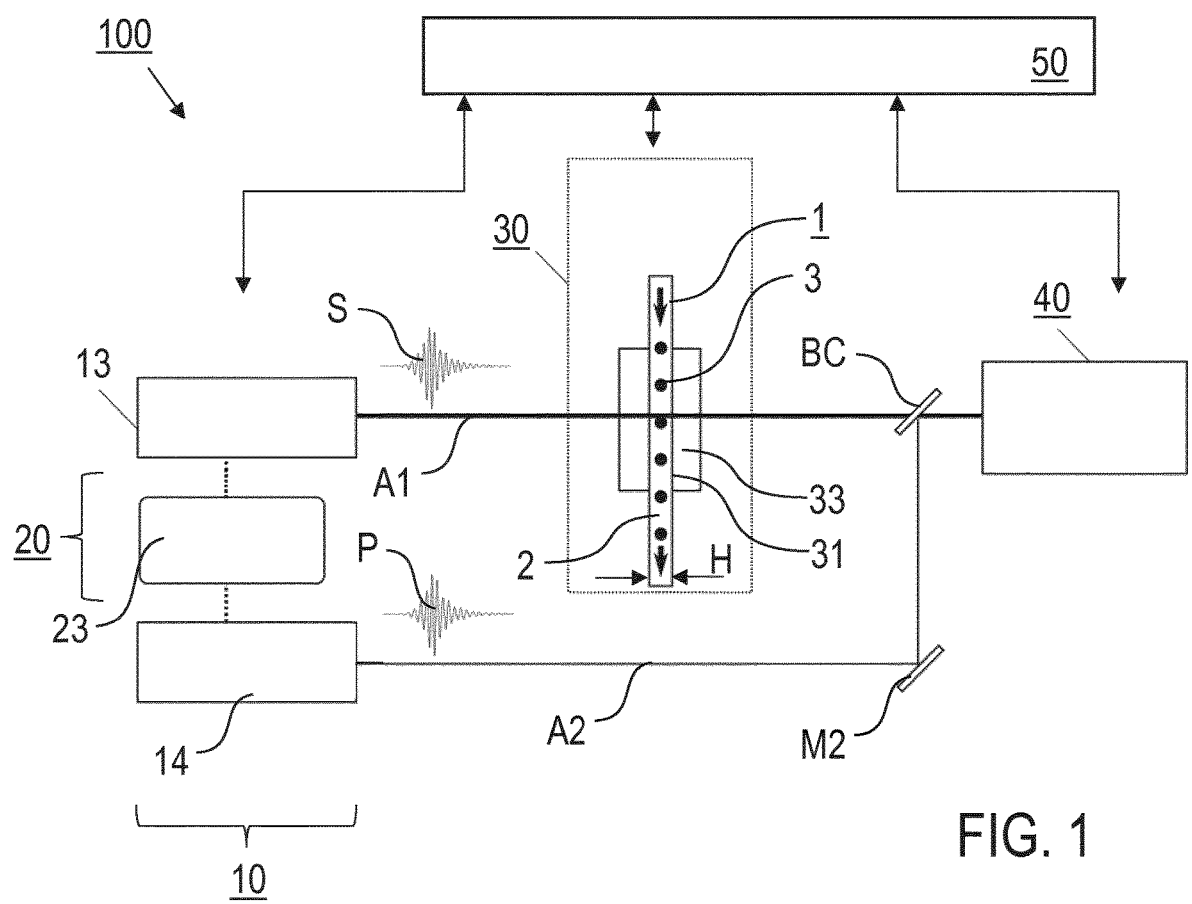
FIG. 1: a general illustration of a particle analysis apparatus according to embodiments of the invention.
Figure 6:
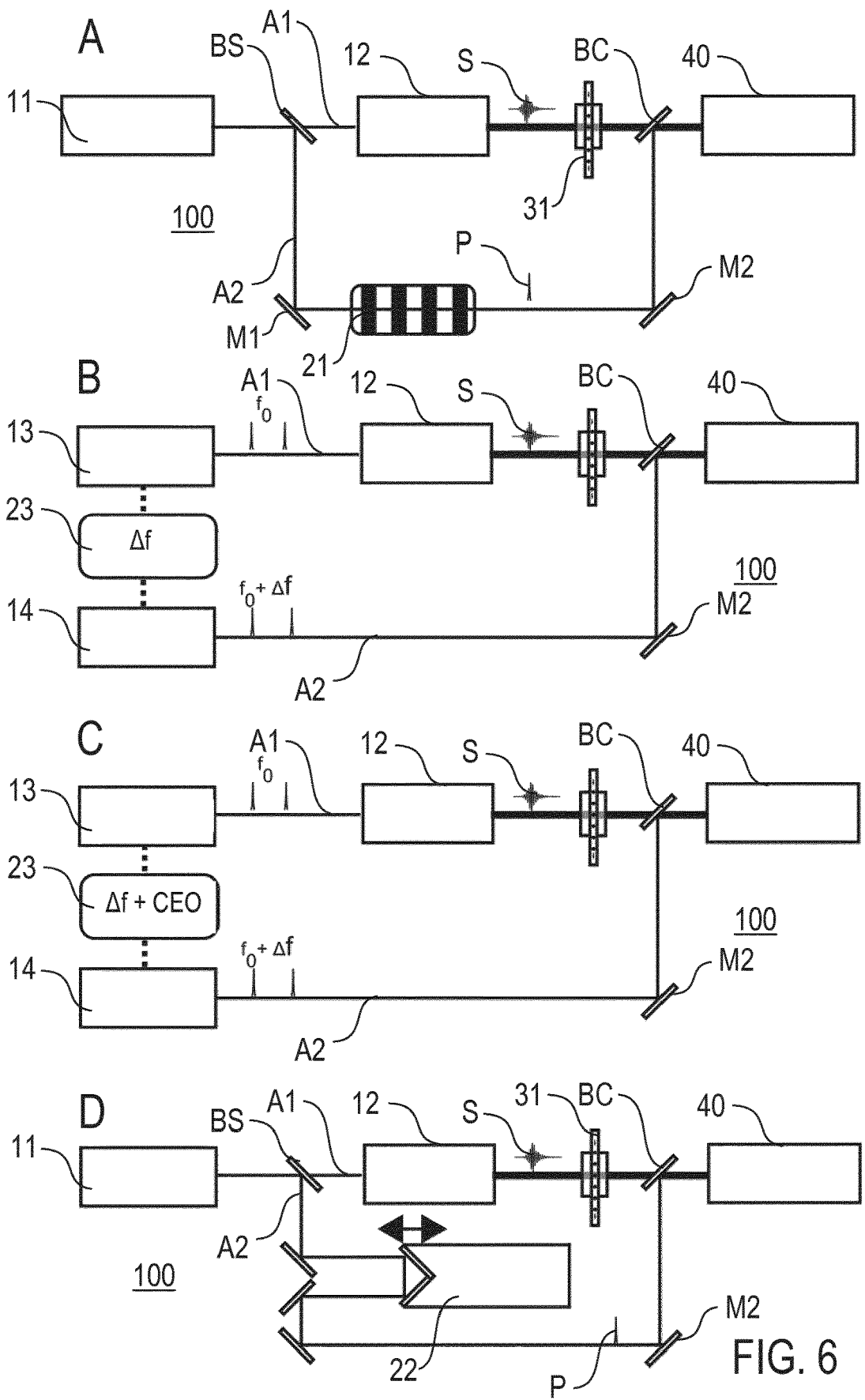
FIG. 6: features of the FRS embodiment of the invention, utilizing a field-resolved detection of the sample light beam.
Figure 7:
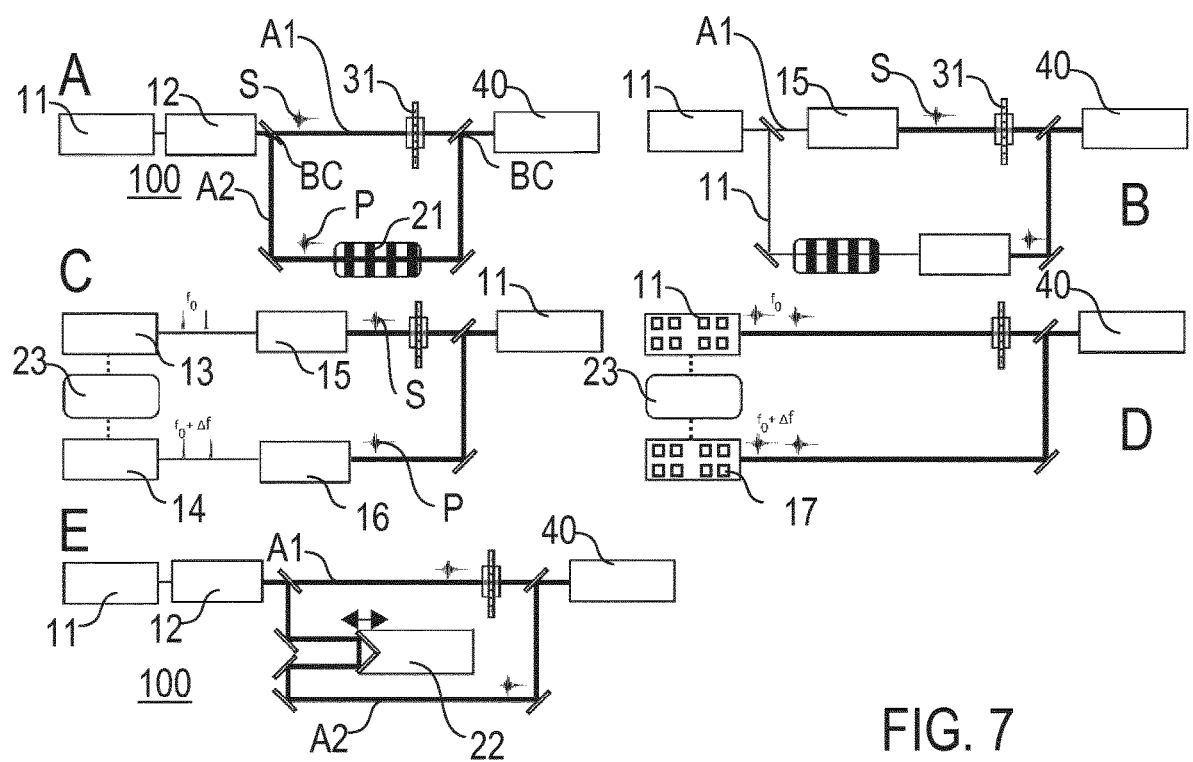
FIG. 7: features of the multi-heterodyne embodiment of the invention, utilizing a heterodyne detection of the sample light beam.

FIG. 1 schematically shows a particle analysis apparatus 100 with a light source device 10, a phase modulator device 20, a fluidic device 30, a detector device 40 and a control device 50. The light source device 10, the phase modulator device 20 and the detector device 40 are configured with various laser sources and optionally frequency conversion devices in dependency on the detection principle used, e. g. as described in detail below with reference to FIGS. 6 and 7.

The fluidic device 30 comprises a complete fluid handling system (not shown in detail) as it is known per se e. g. from conventional flow cytometry devices, in particular including a flow through cuvette 33, a sample reservoir (not shown) and a flow drive device (not shown). The flow drive device is adapted for pumping the sample from the sample reservoir through the sample channel and for adjusting the particle speed in the sample channel 31. The particle speed is controlled with the control device 50 in particular in dependency on the available detection rate (scan speed of the phase modulator device 20) and the available signal to noise generated by the detector device 40. A fluid sample 1 including a sheath fluid 2 with particles 3 is pumped through the flow through cuvette 33. The density of the particles is set such that single particles cross the beam path A1 of the sample light beam S. Deviating from conventional flow cytometry devices, the flow through cuvette 33 provides a sample channel 31 with a channel height H along the beam path A1 with H≤100 µm. The walls of the sample channel 31 e. g. are made of an MIR transparent material, like germanium, zinc selenide or calcium fluoride. Another constraint arises from the absorption of water in the MIR region. For optimal signal-to-noise ratio the height H of the sample channel 31 preferably is 2/α with α being the absorptivity of the liquid in which the particle is embedded. In the case of water at a wavelength of 10 µm, the optimal height would be approximately 30 µm. A maximum thickness of 50 µm would be desirable, but larger heights, e. g. up to 100 µm are possible as well. The walls of the sample channel 31 can be arranged under Brewster's angle relative to the beam path for dispersion compensation.

The control device 50 comprises one or more control units being coupled in particular with the components 10, 20, 30 and 40. Furthermore, the control device 50 includes a calculation device providing a particle property on the basis of the detected spectral response of the particle.

With the light source device 10 including two pulsed laser sources 13, 14, a sample light beam S and a probe light beam P are created. The first pulsed laser source 13 comprises a fs pulse laser emitting in an NIR spectral range (between 8400 $cm^{-1}$ and 10700 $cm^{-1}$, or 8000 $cm^{-1}$ and 12000 $cm^{-1}$, or 3000 $cm^{-1}$ and 6000 $cm^{-1}$) and an MIR generation device as described below. The second pulsed laser source 14 comprises a fs pulse laser as well. The phase modulator device 20 comprises a repetition rate control device 23 being connected with the fs pulse lasers and setting a controlled and rapidly changing phase relation of the probe light beam P relative to the sample light beam S. The phase modulator device 20 varies the relative phase with a scanning period equal to or below the irradiation period of irradiating the at least one particle 3. The sample light beam S is directed on a first interferometer arm A1 via the sample channel 31 and a beam combiner BC to the detector device 40. The probe light beam P is directed without a sample interaction along a second interferometer arm A2 via a deflection mirror M2 and the beam combiner BC to the detector device 40. The beam combiner BC comprises e. g. a semi-transmissive mirror or a dichroic mirror. The detector device 40 is adapted for infrared light detection with fast read-out electronics.

The broadband and intense sample light beam S from the pulsed MIR laser source 13 is passed through the measurement volume in the flow-through cuvette 33. The sample light beam S is recombined with the probe light beam P after the interaction with the fluid sample 1, and the combined beams are sent to the detector device 40. The output signal of the detector device 40 being obtained by changing the relative phase relation between sample and probe light beams S, P is used to reconstruct the optical spectrum of the sample light beam S. By comparing the optical spectrum of the sample light beam S in absence and presence of a particle 3, the absorption and phase spectrum of the particle 3 can be retrieved which may be used to determine at least one property of the particle 3.

The detector device 40, including a fast photodiode (conversion of optical signals into electrical signals) and the control device 50 preferably are adapted for fast read-out electronics and data handling. To this end, they include read-out electronics and computing circuits, like an amplifier for the photodiode, a fast analog-to-digital converter and a computer.

In general, the MIR spectrum of a particle 3 can be acquired by comparing the MIR spectrum of the sample light beam S with and without the particle 3. According to the invention, this is a dynamic process as the particle is moving while the spectra are taken. This process is shown schematically in FIG. 2, wherein illustrations A to E show a time series of measurements conducted while a particle 3 crosses an irradiation position P1, where the sample light beam S crosses the sample channel 31. The left curves show sample light beam spectra provided by the output of the detector device 40, and the right curves show referenced absorption spectra of a particle to be analyzed (phase spectra not shown).

In the case of no particle being within the sample light beam S (FIG. 2A), the Fourier transform of the detector output yields a so-called reference spectrum determined by the spectral features of the sample light beam S and the first interferometer arm A1, including the walls of the sample channel 31 and the sheath fluid. All subsequent spectra that are recorded may be referenced to this reference spectrum and a difference between a spectrum measured with a particle at the irradiation position P1 and the reference spectrum is expressed as an absorption and phase spectrum of the particle. As soon as a particle starts to enter the beam waist of the sample light beam S, the acquired subsequent spectra start to differ from the reference spectrum and one observes an emerging absorption pattern in the absorption spectrum (FIG. 2B). The pattern gets stronger until the particle has fully entered the beam path (FIG. 2C) and eventually decreases as the particle is exiting the beam waist. At the end of one measurement event, there is no particle present within the beam path anymore, and the absorption spectrum is close to zero again (FIG. 2E). This procedure is repeated for any subsequent particle.

The series of thusly acquired multiple spectra per particle can be used to determine the absorption and phase spectrum of the particle to be obtained. As a first approximation, the spectrum of the series with the strongest absorption (e. g. according to FIG. 2C) can be considered to be closest to the actual absorption spectrum of the particle. To increase the signal-to-noise ratio, several spectra of the series may be averaged. Additionally, at least one spectral correction procedure may be applied to eliminate artefacts in the spectrum (for example due to MIE-scattering, see e. g. [4]).

The spectral correction algorithm may use additional information on the particles, like e. g. the particle size. The particle size can be provided as pre-known information on the particles (resulting from pre-processing steps or pre-knowledge on the sample investigated) and/or as a result of an additional flow cytometry measurement conducted with the same fluidic device 30 or an additional flow cytometry device (not shown). Particle features obtained with the additional flow cytometry measurement can be used to improve the spectral corrections algorithms for the MIR spectra. Additionally or alternatively, they can be used to temporally gate the acquisition of the MIR spectra, and/or to improve the determination of particle properties.

Figure 2:
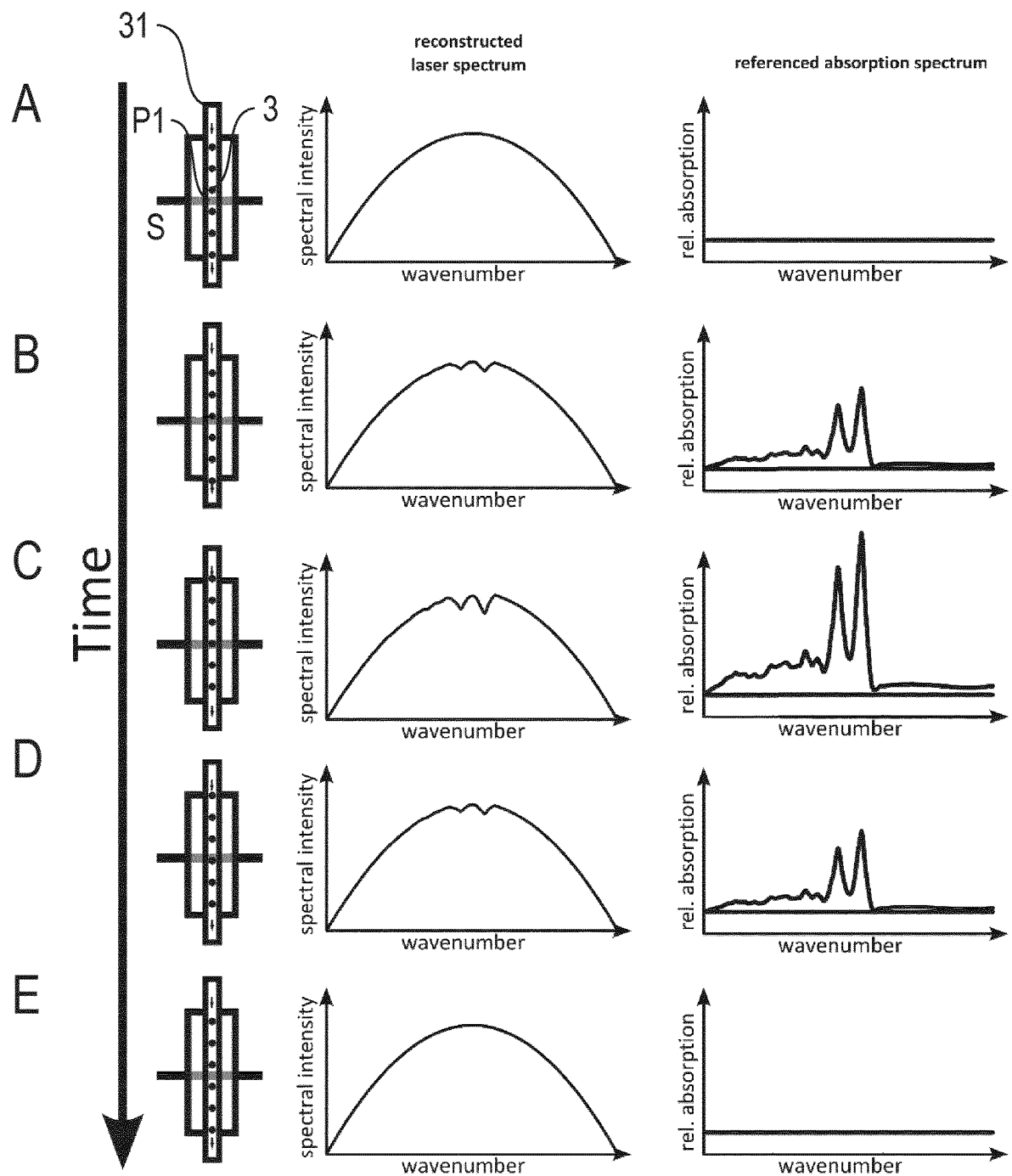
FIG. 2: a flowchart of an acquisition of a spectral response of a particle with a particle analysis method according to embodiments of the invention.

As an alternative to FIG. 2, only one spectrum is measured per particle, which provides the particle spectrum after comparing/referencing the reference spectrum, e. g. dividing by the reference spectrum. A spectral correction procedure can be applied in this case as well.

According the invention, at least one particle property of the at least one particle is determined based on the spectral response measured with the detector device 40. Infrared spectroscopy is sensitive to chemical bonds and therefore sensitive to the biochemical composition of the investigated sample. Certain absorption peaks in a spectrum of a particle can be assigned and attributed to specific molecular classes, like proteins, lipids, nucleic acids or carbohydrates. An overview and description of typical evaluation approaches of IR spectra as well as potential properties that can be extracted is given in [5] and [6]. The data evaluation strategy of the proposed invention may be similar to the approaches described in the references given above.

Figure 3:
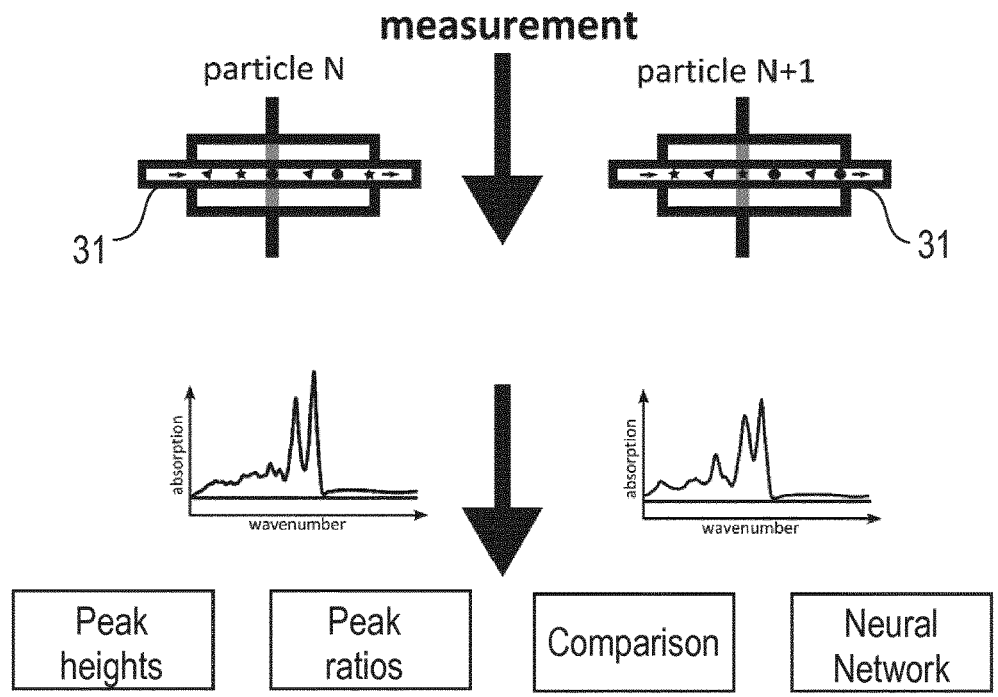
FIG. 3: an illustration of determining particle properties of a particle.

Preferably, the at least one particle property is determined as described in the following. According to FIG. 3, it is schematically shown how the spectra of different particles are measured and how different properties may be assigned. In a first step the spectra of the particles are acquired as described above and spectral correction algorithm may be used to reconstruct the particle spectra. Next, the acquired particle spectra and possibly any additional information acquired by conventional flow cytometry techniques (e.g. forward and side scattering) may be used to determine at least one property of the particle. For example, subsequent different particles N and N+1 have different spectral responses, being measured with the procedure of FIG. 2 and being specific for a certain cell type. The particle property to be obtained can be provided directly from quantitative features of the measured spectral response or indirectly by applying a numerical algorithm on the spectra.

As a first alternative, an analysis of the total absorption of those peaks (peak heights) and/or the peak ratios (quotients of peak heights), can provide information about the basic chemical composition (e.g. total protein content) or physical features (e. g. size) of the investigated particle.

Alternatively, the particle property can be obtained by a numerical algorithm including a comparison of the measured spectra with spectra from a database including spectra of known substances and/or cells.

A more sophisticated numerical analysis of the acquired spectra applying a machine learning algorithm (like artificial neural networks or support vector machines) can be used to determine at least one property of the particle. This includes the determination and quantification of certain substances within the particles (e.g. glucose content of cells), conformation of proteins within the particle and the identification of the particle type. For the example of living cells, the cell (sub-) type and phenotype can be identified using the IR spectrum in combination with computational analysis. Typically, a machine learning algorithm would use a training set, consisting of a large number of measured spectra of particles with known properties. Those spectra would be used to train the machine learning algorithm to recognize certain spectral features and link them with certain properties. Afterwards, the algorithm can be used to assign properties to new measured particles based on this training set. With increased number of training data, the algorithm tends to get more accurate. Additional information about the particle (e.g. particle size) acquired with conventional flow cytometry methods (forward and side scattering) may be used to improve the accuracy and effectiveness of the machine learning algorithm.

The above alternatives can be applied in any combination. Additional information acquired by a flow cytometry technique can be used for evaluating the particle spectra, e. g. for separating single cells and cell aggregates.

Diagnostically relevant information is derived from the particle property. For example, if tumour cells are detected, the directly represent an indication for a subsequent diagnosis. Similarly, chemical components within the cells can be specific for diseases, which can be identified with a subsequent diagnosis.

Figure 4:
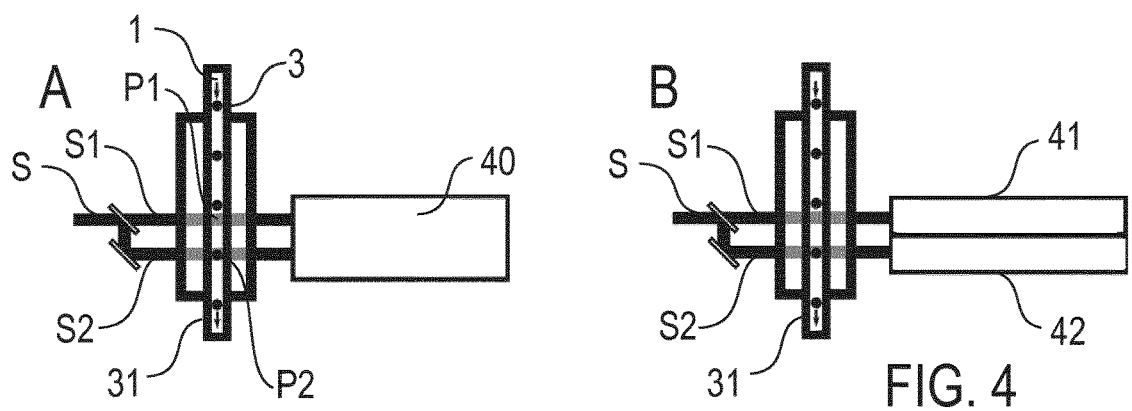
FIG. 4: an embodiment of a reference measurement.

FIG. 4 illustrates an embodiment of the invention, wherein a reference measurement is conducted for increasing the SNR and/or the measuring rate of the particle analysis. As shown in FIG. 2A, a reference spectrum can be acquired by measuring the sample channel 31 including the sheath fluid but not a particle at the irradiation position. With the reference measurement embodiment of FIG. 4, this can be done by simultaneously using two partial sample light beams S1, S2, which are copies of the initial sample light beam S. The partial sample light beams S1, S2 irradiate the fluid sample 1 at irradiation positions P1, P2, that are displaced by a least one diameter of the particle 3.

According to a first variant, the sample spectrum is obtained by subtracting both beams optically and measuring the difference with one common detector device 40 (see FIG. 4A). A detailed description of this variant, but with a stationary, not-flowing sample, is disclosed in [3]. The output of the detector device 40 directly represents the spectral response of the particle 3. According to a second variant, both partial sample light beams S1, S2 are analyzed with independent detection units 41, 42 (either based on FRS detection or heterodyne detection, see FIGS. 6 and 7) to acquire the reference and sample spectra simultaneously (see FIG. 4B). The spectral response of the particle 3 is obtained by subtracting the output of the detector unit sensing the sheath fluid alone (spectral reference response) from the output of the other detector unit sensing the particle 3. One advantage of these two variants is that potential drifts over time between reference and sample measurement can be excluded, as both are recorded at the same time. Additionally, the implementation with two sample light beams and two detection units 41, 42 means that the spectral acquisition is redundant and therefore less prone to measurement errors and artefacts.

Figure 5:
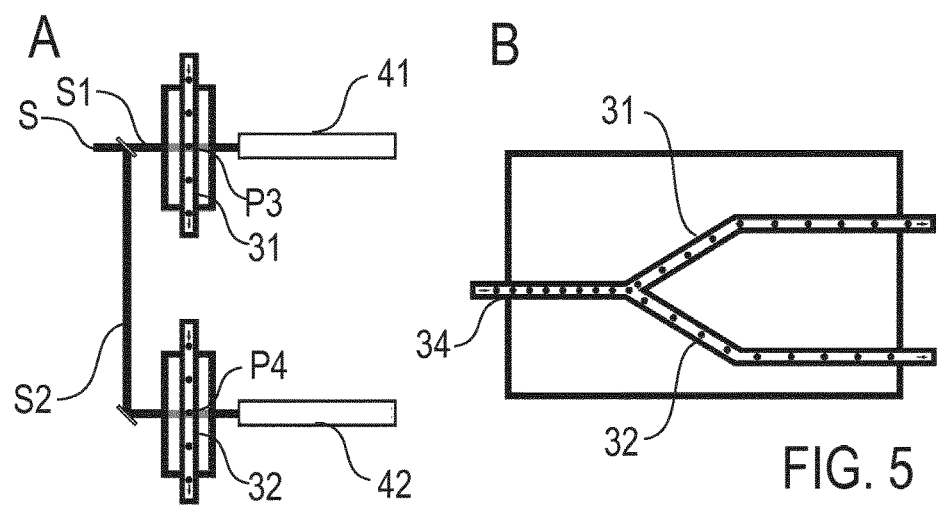
FIG. 5: an embodiment of a parallel measurement.

According to further variants, the reference measurement can be conducted with multiple sample channels 31, 32, as illustrated in FIG. 5 (parallel measurement). According to FIG. 5A, the sample channels 31, 32 are channels each being connected with a separate sampler reservoir (not shown). The sample channels 31, 32 are irradiated at separate irradiation positions P3, P4 with partial sample light beams S1, S2 being split from a common initial sample light beam S. According to FIG. 53 (shown without the sample light beams and detection units), the fluidic system can be designed with several sample channels 31, 32 being connected in parallel on a single chip. An input sample channel 34 is connected via a fluid splitter with the sample channels 31, 32. After passing through the sample channels 31, 32, each partial sample light beam S1, S2 is detected independently by a detection unit 41, 42 (either based on FRS detection or heterodyne detection, see FIGS. 6 and 7).

The parallel measurement can be utilized for increasing the throughput of the particle analysis, wherein in particular more than two sample channels are provided. The parallel measurement can be conducted with or without the reference measurement. The reference measurement can be integrated by using at least one of the sample channels for the sensing the spectral reference response of the sheath fluid (as shown in FIG. 5) or by providing one of the setups of FIG. 4 at at least one of the sample channels.

Variants of the FRS embodiment of the invention (detection based on field-resolved spectroscopy, FRS) are illustrated in FIGS. 6A to 6D. These variants have in common that the detection of MIR light of the sample light beam(s) is based on field-resolved-spectroscopy via electro-optical sampling (see e. g. [2]). This has the advantage that fast, sensitive and cheap detectors can be used. The broadband, intense mid-infrared (MIR) sample light beam S is usually generated via difference-frequency generation using a short intense driving pulse in the near-infrared (NIR). The probe light beam P may be a copy of the driving pulse of the difference-frequency generation or originate from a second laser source. There are different options to introduce a fast and controllable phase delay between sample and probe light beams S, P.

According to FIG. 6A, the light source device comprises a laser source 11, like e. g. a Yb:YAG laser emitting a train of laser pulses with a duration of e. g. 250 fs, a repetition rate of 25 MHz and a centre wavelength at 1.03 µm, combined with a pulse compressor compressing the pulse duration to 15 fs. The output of this single laser oscillator/compressor is split with a beam splitter BS into two interferometer arms A1, A2. The first interferometer arm A1 includes the MIR generation device 12 and the sample channel 31. The MIR generation device 12 is configured for creating the sample light beam S as a train of laser pulses with a duration of e. g. 80 fs and an MIR centre wavelength of e. g. 8 µm by difference frequency generation (DFG). The DFG uses frequency components of the output from the laser source 11 for creating the sample light beam S, which passes through the sample channel 31.

The pulses of the probe light beam P are directly provided by the output from the laser source 11. Along the second interferometer arm A2, the probe light pulses P are directed via a first deflecting mirror to an acousto-optical delay line 21. The acousto-optical delay line 21 comprises a dazzler, which is used for acousto-optically delaying the probe light beam P, i. e. the pulses thereof, relative to the sample light beam pulses. Accordingly, the relative phase between the sample and probe light beam pulses is varied from pulse to pulse. The scanning period is selected to be equal to or below the irradiation period of irradiating the at least one particle in the sample channel 31. The acousto-optical delay line 21 provides e. g. up to 9 ps delay with 100 k scans per second being adapted to an irradiation period at the particle 3 of e. g. 0.1 ms. The acousto-optical delay line 21 is configured e. g. as described in [7]. Subsequently, the probe light beam P is recombined with the sample light beam at the beam combiner BC. The combined beams are directed to the detector device 40 for electro-optic sampling of the field shape of the superimposed sample and probe light beams.

With the variant according to FIG. 6B, an asynchronous optical sampling (ASOPS, see e. g. [10]) is provided. The light source device comprises two laser source 13, 14, each like the laser source 11 of FIG. 6A, but being operated with different repetition rates. The output of the first laser source 13 with a repetition rate $f_0$, e. g. 100 MHz, is converted in the first interferometer arm A1 with the MIR generation device 12 into the MIR sample light beam S, which irradiates the sample channel 31, as described with reference to FIG. 6A. The output of the second laser source 13 with a variable repetition rate $f_0+\Delta f$ provides the NIR probe light beam P. The repetition rate difference $\Delta f$ is scanned with the repetition rate control device 23, including a locking control setting the varying repetition rate difference $\Delta f$. The repetition rate control device 23 can be configured as described e. g. in [8]. The offset between the repetition rates of the first and second laser sources 13, 14 leads to a changing temporal delay between successive pulses. Again, the relative phase between the sample and probe light beam pulses is varied from pulse to pulse. When a total offset T, e. g. 5 ps to 10 ps ms is reached, the repetition rate control device 23 sets back the repetition rate difference $\Delta f$ to zero, and a new scan begins. Like in FIG. 6A, the sample and probe light beams S, P are recombined at the beam combiner BC and directed to the detector device 40 for electro-optic sampling.

FIG. 6C shows a variant of the FRS embodiment, which substantially has the same structure like FIG. 6B. In this case, the particle spectrum is sensed by dual-comb-spectroscopy (see e. g. [11]) with down-conversion using the MIR generation device 12 of one interferometer arm A1. The repetition rate and carrier envelope offset phase control device 23 of FIG. 6C is adapted for controlling the varying repetition rate difference $\Delta f$ and the carrier envelope offset phase of the two laser source 13, 14.

According to the variant of FIG. 6D, an ultrarapid-scanning interferometer is provided. This set-up is corresponds to the variant of FIG. 6A, wherein the acousto-optical delay line 21 is replaced by a mechanical manner, comprising a sonotrode 22. The sonotrode 22 can be configured as described in [9].

Variants of the multi-heterodyne embodiment of the invention (detection of the spectral response by a multi-heterodyne detection of the sample and probe light beams in the MIR) are illustrated in FIGS. 7A to 7E. With the multi-heterodyne embodiment, the detection of the MIR-light is performed with MIR-detectors. The detector device 40 includes a signal evaluation circuit, analyzing a difference or beat frequency produced by the detector for providing the spectral response of the particle. Preferably, the detector device 40 comprises a mercury cadmium telluride (MCT)-detector. For optimum performance, the probe light beam P preferably has beam properties and spectral coverage being matched or equal to the sample light beam S. Depending on how the probe light beam P is generated, there are different options to introduce the fast and controllable phase delay between the two beams S, P.

According to FIG. 7A, the light source device comprises a laser source 11 and an MIR generation device 12 (configured like in FIG. 6A). The output of the MIR generation device 12 is split with a beam splitter BS into two interferometer arms A1, A2. The first interferometer arm A1 includes the sample channel 31. A first portion of the output of the MIR generation device 12 is directed as the sample light beam S along the first interferometer arm A1, and second portion of the output of the MIR generation device 12 is directed as the probe light beam P along the second interferometer arm A2. In the second interferometer arm A2, the probe light pulses P are directed via a first deflecting mirror to an acousto-optical delay line 21 (configured like in FIG. 6A) and via a second deflecting mirror to the beam combiner BC. Subsequently, the probe light beam P is recombined with the sample light beam at the beam combiner BC. The combined beams are directed to the detector device 40 for balanced multi-heterodyne detection in the MIR wavelength range.

FIG. 7B shows a modification of the variant of FIG. 7A, wherein the NIR output beam of the laser source 11 firstly is split into the interferometer arms A1, A2. In the first interferometer arm A1, the first MIR generation device 15 creates the sample light beam S irradiating the sample channel 31. In the second interferometer arm A2, firstly the variable optical delay is introduced with the acousto-optical delay line 21, followed by the same MIR generation process with the second MIR generation device 16.

According to FIG. 7C, the particle analysis apparatus can be configured similar to the variant of FIG. 6B. The first laser source 13 is combined in the first interferometer arm A1 with the first MIR generation device 15 for creating the sample light beam S. For the multi-heterodyne detection in the MIR wavelength range, the probe light beam P is created with the second MIR generation device 16 driven by the second laser source 14. The varying relative phase delay between the sample and probe light beams S, P is created with the repetition rate control device 23, as described with reference to FIG. 6B.

While the MIR radiation is generated via frequency conversion of the output of both laser sources in the variant of FIG. 7C, direct MIR frequency comb-spectroscopy can be conducted according to FIG. 7D. With this variant, the combinations of a laser source and an MIR generation device are replaced by single QCLs 17 or groups of multiple QCLs 17, being locked with the varying relative phase delay via the repetition rate control device 23. As an example, 4 QCLs 17 are provided per channel, wherein the superimposed output of the QCLs 17 covers the broadband MIR range to be obtained.

Finally, FIG. 7E shows a variant of an ultrarapid-scanning interferometer, which is configured in analogy to FIG. 6D. The output of the MIR generation device 12 driven by the laser source 11 is split into the first and second interferometer arms A1, A2, wherein the varying phase delay between the sample and probe light beams S. P is introduced with the sonotrode 22, preferably having a modulation frequency of at least 500 Hz.

With a further modification of the invention, groups of QCLs 17 also can be used with the variants of FIG. 7A, B or E.

The features of the invention disclosed in the above description, the drawings and the claims can be of significance individually, in combination or sub-combination for the implementation of the invention in its different embodiments.

The invention claimed is:
1. A particle analysis method, including a spectrometry-based analysis of a fluid sample comprising a sheath fluid and at least one particle be analyzed, comprising the steps of
creating a sample light beam and a probe light beam with a light source device and periodically varying a relative phase between the sample and probe light beams with a phase modulator device,
irradiating the fluid sample with the sample light beam, whereas the fluid sample is flowing in at least one sample channel through a beam path of the sample light beam, so that the at least one particle is irradiated for a predetermined irradiation period, detecting the fluid sample and the sample light beam and the probe light beam with a detector device, and providing a spectral response of the at least one particle based on an output of the detector device, wherein the light source device comprises at least one broadband source, which has an emission spectrum covering a mid-infrared (MIR) frequency range, and the phase modulator device varies the relative phase with a scanning period equal to or below the irradiation period of irradiating the at least one particle.

2. The particle analysis method according to claim 1, wherein a particle property of the at least one particle is determined based on the spectral response of the at least one particle.

3. The particle analysis method according to claim 2, wherein the particle property of the at least one particle comprises at least one of a chemical composition of the particle, a physical condition of the particle, a cell type of a biological cell in a circulation of a biological organism, and at least one of a healthy cell, a tumor cell and a stem cell.

4. The article analysis method according to claim 1, wherein the detector device is configured for a field-resolved detection of the sample light beam by electro-optical sampling.

5. The article analysis method according to claim 4, wherein the light source device comprises a laser source coupled with a MIR generation device, an output of the laser source is split into a first interferometer arm, including the MIR generation device and the at least one sample channel and a second interferometer arm including the phase modulator device, the sample light beam created with the laser source and the MIR generation device and the sample is irradiated in the first interferometer arm, the probe light beam is created with the laser source and directed along the second interferometer arm, the relative phase between the sample and probe light beams is controlled with the phase modulator device the second interferometer, and after an interaction of the sample light beam with the sample, the sample and probe light beams are recombined for the field-resolved detection of the sample light beam.

6. The particle analysis method according to claim 5, wherein the phase modulator device comprises an acousto-optical delay line or a mechanical phase modulator.

7. The particle analysis method according to claim 4, wherein the light source device comprises a first pulsed laser source and a second pulsed laser source, the phase modulator device comprises a repetition rate control device coupled with the first and second pulsed laser sources, the sample light beam is created with the first pulsed laser source, the probe light beam is created with the second pulsed laser source, the relative phase between the sample and probe light beams is controlled with the repetition rate control device, and after an interaction of the sample light beam with the sample, the sample and probe light beams are recombined for the field-resolved detection of the sample light beam.

8. The particle analysis method according to claim 7, wherein the first pulsed laser source is coupled with a MIR generation device creating the sample light beam.

9. The article analysis method according to claim 7, wherein the repetition rate control device further controls a carrier-envelope offset phase of the first and second pulsed laser sources.

10. The particle analysis method according to claim 1, wherein the detector device is configured for multi-heterodyne detection of the sample light beam in the MIR frequency range.

11. The particle analysis method according to claim 10, wherein the light source device comprises a laser source coupled with a MIR generation device, an output of the laser source or the MIR generation device is split into a first interferometer arm including the at least one sample channel and a second interferometer arm including the phase modulator device, the sample light beam is created with the laser source and the MIR generation device and the sample is irradiated in the first interferometer arm, the probe light beam is created with the laser source or the MIR generation device and directed along the second interferometer arm, the relative phase between the sample and probe light beams is controlled with the phase modulator device the second interferometer arm and after an interaction of the sample light beam with the sample, the sample and probe light beams are recombined for the multi-heterodyne detection of the sample light beam in the MIR frequency range.

12. The particle analysis method according to claim 11, wherein the phase modulator device comprises an acousto-optical delay line or a mechanical phase modulator.

13. The particle analysis method according to claim 10, wherein the light source device comprises multiple MIR lasers, an output of the MIR lasers is split into a first interferometer arm including the at least one sample channel and a second interferometer arm including the phase modulator device, the sample light beam is created with the MIR lasers and the sample is irradiated in the first interferometer arm, the probe light beam is created with the MIR lasers and directed along the second interferometer arm, the relative phase between the sample and probe light beams is controlled with the phase modulator device the second interferometer arm, and after an interaction of the sample light beam with the sample, the sample and probe light beams are recombined for the multi-heterodyne detection of the sample light beam in the MIR frequency range.

14. The particle analysis method according to claim 13, wherein
the phase modulator device comprises an acousto-optical delay line or a mechanical phase modulator.

15. The particle analysis method according to claim 10, wherein
the light source device comprises a first pulsed laser source coupled with a first MIR generation device and a second pulsed laser source coupled with a second MIR generation device or multiple MIR lasers,
the phase modulator device comprises a repetition rate and carrier-envelope offset phase control device coupled with the first and second pulsed laser sources or multiple MIR lasers,
the sample light beam is created with the first MIR generation device,
the probe light beam is created with the second MIR generation device,
the relative phase and the carrier-envelope offset phase between the sample and probe light beams are controlled with the repetition rate and carrier-envelope phase offset control device, and
after an interaction of the sample light beam with the sample, the sample and probe light beams are recombined for the multi-heterodyne detection of the sample light beam in the MIR frequency range.

16. The particle analysis method according to claim 1, further comprising a reference measurement, wherein
the step of irradiating the fluid sample with the sample light beam includes irradiating the sheath fluid in absence of any particle for the predetermined irradiation period,
the sample and probe light beams are detected with the detector device, and
a spectral reference response of the sheath fluid is provided, based on an output of the detector device.

17. The particle analysis method according to claim 16, wherein
the reference measurement is conducted at two irradiation positions being separated from each other along the at least one sample channel, so that a particle can be in at most one position of the two irradiation positions.

18. The particle analysis method according to claim 17, wherein
the irradiation positions are separated by a spacing equal to 1 to 2 diameters of the particle to be analyzed or by a beam diameter of the sample light beams at the irradiation positions.

19. The particle analysis method according to claim 16, wherein
the reference measurement is conducted at two irradiation positions being included in different sample channels.

20. The particle analysis method according to claim 1, further comprising a parallel measurement in multiple sample channels, including
flowing the fluid sample through a first sample channel and at least one further sample channel, and
irradiating the fluid sample with the sample light beams through split sample light beam paths of the sample light beams, so that a first particle is irradiated for a predetermined irradiation period in the first sample channel and at least one further particle is irradiated for a predetermined irradiation period in the at least one further sample channel,
detecting the sample and probe light beams of the first and at least one further sample channels with the detector device,
providing a first spectral response and at least one further spectral response of the particles, based on the output of the detector and
determining the particle properties of the first and at least one further particles, based on the first and at least one further spectral responses of the first and at least one further particles.

21. The particle analysis method according to claim 20, including
providing a differential spectral response between the first spectral response and a second spectral response of the particles.

22. The particle analysis method according to claim 1, wherein
the emission spectrum of the at least one broadband source covers a frequency interval of at least 30 cm$^{-1}$, within a frequency range from 100 cm$^{-1}$ to 4000 cm$^{-1}$.

23. The particle analysis method according to claim 1, wherein
the light beam irradiating the sample has an output power equal to or above 0.1 mW.

24. The particle analysis method according to claim 1, wherein
the at least one broadband source is stably operated and the fluid sample is investigated in a continuous operation mode without heating of particles.

25. The particle analysis method according to claim 1, wherein
the at least one particle has a cross-sectional dimension below 100 μm.

26. The particle analysis method according to claim 1, wherein
the fluid sample includes a biological sample and the at least one particle comprises at least one biological cell, a cell group or a component of a cell.

27. The particle analysis method according to claim 1, further including a step of
fluid sample and particle handling, including controlling at least one of time of flowing the fluid sample through the sample channel, flow velocity of the fluid sample through the sample channel, and density of particles within the fluid sample.

28. The particle analysis method according to claim 1, wherein
the fluid sample has a flow velocity in a range from 0.1 mm/s to 100 mm/s.

29. The particle analysis method according to claim 1, including a step of
collecting diagnostically relevant information.

30. The particle analysis method according to claim 1, further including
sorting of the particles in dependency on the spectral response thereof.

31. The particle analysis method according to claim 1, wherein
the particle analysis of the fluid sample comprises a high-throughput measurement.

32. The particle analysis method according to claim 1, wherein
the particle analysis of the fluid sample is combined with an additional flow cytometry measurement.

33. A particle analysis apparatus, being configured for a spectrometry-based analysis of a fluid sample comprising a sheath fluid and at least one particle to be analyzed, comprising
a light source device being configured for creating a sample light beam and a probe light beam, a phase modulator device being configured for periodically varying a mutual relative phase between the sample light beam and the probe light beams,
at least one sample channel being arranged for accommodating a flow of the fluid sample and for irradiating the fluid sample with the sample light beam, so that the at least one particle is irradiated for a predetermined irradiation period, and
a detector device being configured for detecting the sample light beam and the probe light beam and providing a spectral response of the at least one particle, wherein
the light source device comprises at least one broadband source, which has an emission spectrum covering a mid-infrared (MIR) frequency range, and
the phase modulator device is configured for varying the mutual relative phase with a scanning period equal to or below the irradiation period of irradiating the particles.

34. The particle analysis apparatus according to claim 33, wherein
the detector device is configured for a field-resolved detection of the sample light beam by electro-optical sampling.

35. The particle analysis apparatus according to claim 34, wherein
the light source device comprises a laser source coupled with a MIR generation device,
an output of the laser source is split with a beam splitter device into a first interferometer arm, including the MIR generation device and the sample channel, and a second interferometer arm including the phase modulator device,
the laser source and the MIR generation device are arranged for creating the sample light beam and directing it along the first interferometer arm,
the laser source is arranged for creating the probe light beam and directing it along the second interferometer arm,
the phase modulator device is arranged in the second interferometer arm for controlling the mutual relative phase between the sample and probe light beams, and
after passing the sample channel, the sample and probe light beams are recombined with a beam combiner device for the field-resolved detection of the sample light beam.

36. The particle analysis apparatus according to claim 35, wherein
the phase modulator device comprises an acousto-optical delay line or a mechanical phase modulator.

37. The particle analysis apparatus according to claim 34, wherein
the light source device comprises a first pulsed laser source and a second pulsed laser source,
the phase modulator device comprises a repetition rate control device coupled with the first and second pulsed laser sources,
the first pulsed laser source is arranged for creating the sample light beam,
the second pulsed laser source is arranged for creating the probe light beam,
the repetition rate control device is arranged for controlling the relative phase between the sample and probe light beams, and
after passing the sample channel, the sample and probe light beams are recombined with a beam combiner device for the field-resolved detection of the sample light beam.

38. The particle analysis apparatus according to claim 37, wherein
the first pulsed laser source is coupled with a MIR generation device which is arranged for creating the sample light beam.

39. The particle analysis apparatus according to claim 37, wherein
the repetition rate control device is further arranged for controlling a carrier-envelope offset phase of the first and second pulsed laser sources.

40. The particle analysis apparatus according to claim 33, wherein
the detector device is configured for multi-heterodyne detection of the sample light beam in the MIR frequency range.

41. The particle analysis apparatus according to claim 40, wherein
the light source device comprises a laser source coupled with a MIR generation device,
an output of the pulsed laser source or the MIR generation device is split with a beam splitter device into a first interferometer arm including the sample channel and a second interferometer arm including the phase modulator device,
the laser source and the MIR generation device are arranged for creating the sample light beam and directing it along the first interferometer arm,
the laser source or the MIR generation device is arranged for creating the probe light beam and directing it along the second interferometer arm,
the phase modulator device is arranged in the second interferometer arm for controlling the relative phase between the sample and probe light beams, and
after passing the sample channel, the sample and probe light beams are recombined with a beam combiner device for the multi-heterodyne detection of the sample light beam in the MIR frequency range.

42. The particle analysis apparatus according to claim 41, wherein
the phase modulator device comprises an acousto-optical delay line or a mechanical phase modulator.

43. The particle analysis apparatus according to claim 40, wherein
the light source device comprises multiple MIR lasers,
an output of the MIR lasers is split with a beam splitter device into a first interferometer arm including the sample channel and a second interferometer arm including the phase modulator device,
the MIR lasers are arranged for creating the sample light beam and directing it along the first interferometer arm,
the MIR lasers are arranged for creating the probe light beam and directing it along the second interferometer arm,
the phase modulator device is arranged in the second interferometer arm for controlling the relative phase between the sample and probe light beams, and
after passing the sample channel, the sample and probe light beams are recombined with a beam combiner device for the multi-heterodyne detection of the sample light beam in the MIR frequency range.

44. The particle analysis apparatus according to claim 43, wherein
the phase modulator device comprises an acousto-optical delay line or a mechanical phase modulator.

45. The particle analysis apparatus according to claim 40, wherein
the light source device comprises a first pulsed laser source coupled with a first MIR generation device and a second pulsed laser source coupled with a second MIR generation device,
the phase modulator device comprises a repetition rate and carrier-envelope offset phase control device coupled with the first and second pulsed laser sources,
the first MIR generation device is arranged for creating the sample light beam,
the second MIR generation device is arranged for creating the probe light beam,
the repetition rate and carrier-envelope offset phase control device are arranged for controlling the relative phase and the carrier-envelope offset phase between the sample and probe light beams, and
after passing the sample channel, the sample and probe light beams are recombined with a beam combiner device for the multi-heterodyne detection of the sample light beam the MIR frequency range.

46. The particle analysis apparatus according to claim 33, being configured for a reference measurement, wherein
the light source device is arranged for irradiating the sheath fluid for the predetermined irradiation period,
the detector device is arranged for detecting the sample and probe light beams, and
the particle analysis apparatus is arranged for providing a spectral reference response of the sheath fluid, based on an output of the detector device.

47. The particle analysis apparatus according to claim 46, wherein
the light source device is arranged for irradiating the fluid sample at two irradiation positions being separated from each other along the sample channel.

48. The particle analysis apparatus according to claim 47, wherein
the irradiation positions are separated by a spacing equal to 1 to 2 diameters of the at least one particle to be analyzed.

49. The particle analysis apparatus according to claim 46, wherein
the light source device is arranged for irradiating the fluid sample at two irradiation positions in different parallel sample channels.

50. The particle analysis apparatus according to claim 33, including multiple sample channels and being configured for a parallel measurement in the multiple sample channels, wherein
the multiple sample channels include a first sample channel and at least one further sample channel being connected in parallel relative to the first sample channel, and
the light source device is arranged for irradiating the fluid sample with the sample light beam through split sample light beam paths of the sample light beam, so that a first particle is irradiated for a predetermined irradiation period in the first sample channel and at least one further particle is irradiated for a predetermined irradiation period in the at least one further sample channel,
the detector device is arranged for detecting the sample and reference light beams of the first and at least one further sample channels, and
the detector device is arranged for providing a first spectral response and at least one further spectral response of the particles.

51. The particle analysis apparatus according to claim 50, wherein
the detector device is arranged for providing a differential spectral response from the first spectral response and a second spectral response of the particles.

52. The particle analysis apparatus according to claim 33, comprising at least one of the features
the emission spectrum of the at least one broadband source covers a frequency range from 1000 $cm^{-1}$ to 3000 $cm^{-1}$,
the sample light beam irradiating the sample has an output power equal to or above 0.1 mW,
a stabilization device is provided and configured for stably operating the at least one broadband source, and
a flow drive device is provided and configured for flowing the fluid sample with a flow velocity in a range from 0.1 mm/s to 100 mm/s through the at least one sample channel.

53. The particle analysis apparatus according to claim 33, wherein
the particle analysis apparatus is further configured for providing a particle property of the at least one particle on a basis of the spectral response of the at least one particle.

54. The particle analysis apparatus according to claim 33, wherein the particle analysis apparatus is configured for determining at least one of
a chemical composition of the at least one particle,
a physical condition of the at least one particle,
a cell type of the at least one particle, which is a biological cell in a circulation of a biological organism, and
a healthy cell, a tumor cell and a stem cell.

55. The particle analysis apparatus according to claim 33, further including
a particle sorting device being arranged for sorting of the particles in dependency on the spectral response thereof.

56. The particle analysis apparatus according to claim 33, further including
an additional flow cytometry measurement set-up.

* * * * *